United States Patent [19]

Hertel et al.

[11] Patent Number: 5,044,052
[45] Date of Patent: Sep. 3, 1991

[54] METHOD AND APPARATUS FOR FORMING FLUFF PADS FOR DIAPERS AND THE LIKE

[75] Inventors: James E. Hertel; John Merkatoris, both of Green Bay, Wis.

[73] Assignee: Paper Converting Machine Company, Green Bay, Wis.

[21] Appl. No.: 514,199

[22] Filed: Apr. 25, 1990

[51] Int. Cl.⁵ .................. D04H 1/04; D01G 23/08
[52] U.S. Cl. ........................... 28/105; 19/308; 264/121
[58] Field of Search ............... 19/56, 145.7, 148, 301, 19/304, 308; 28/104-106, 116-130, 140, 158; 26/18.6; 264/121, 304, 517; 425/80.1, 81.1; 604/358

[56] References Cited

U.S. PATENT DOCUMENTS

| | | | |
|---|---|---|---|
| 3,483,051 | 12/1969 | Mesek et al. | 19/308 X |
| 3,857,657 | 12/1974 | Teed | 19/301 X |
| 3,862,867 | 1/1975 | Marshall | 264/121 X |
| 3,939,240 | 2/1976 | Savich | 28/121 X |
| 4,153,977 | 5/1979 | Moser | 19/308 X |
| 4,264,290 | 4/1981 | Dunkerly et al. | 264/121 X |
| 4,598,441 | 7/1986 | Stemmler | 19/148 X |
| 4,666,647 | 5/1987 | Enloe et al. | 19/148 X |
| 4,674,966 | 6/1987 | Johnson et al. | 19/148 X |
| 4,859,388 | 8/1989 | Peterson et al. | 264/121 |
| 4,908,175 | 3/1990 | Angstadt | 264/121 X |

Primary Examiner—Werner H. Schroeder
Assistant Examiner—John J. Calvert
Attorney, Agent, or Firm—Tilton, Fallon, Lungmus & Chestnut

[57] ABSTRACT

A method and apparatus for forming fluff pads and the like wherein fluff particles are drawn from a hammermill through a plurality of ducts through a moving screen under vacuum and wherein the ducts are characterized by reverse bends to densify the particle stream at the outside of the curvature for generally perpendicular deposition on the screen.

6 Claims, 2 Drawing Sheets

METHOD AND APPARATUS FOR FORMING FLUFF PADS FOR DIAPERS AND THE LIKE

BACKGROUND AND SUMMARY OF THE INVENTION

This invention relates to a method and apparatus for forming fluff pads for diapers and the like, and more particularly, to apparatus employing a moving screens—as on a rotating drum and novel ductwork. Fluff forming screens have been known for a considerable time—see, for example, co-owned Pat. No. 3,599,293. This invention provides novel means for depositing the fluff particles on the screen.

Typical fluff forming systems, both drum and wire, use large "boxes" positioned over forming wires. These boxes, or forming hoods, are supplied with a fiber/air mixture (typically 0.005 to 0.03 lb. fiber per cubic foot of air) which is then drawn toward the screen through air flow and gravity forces.

Problems often encountered in these basic forming methods are:

uneven fiber density in the pad;

"clumping" due to air turbulence; i.e., formation of "fiber balls" prior to laydown;

clumping due to rolling or picking of the pad by high velocity air tangent to the screen; i.e., air scrubbing off part of the pad and redepositing it as a clump;

To obtain a high pad integrity it is necessary to have a high air flow through the pad during forming. However, the large volume of the forming box allows air turbulence and instability and, hence, the clumping problems described above. These instabilities are usually seen as eddies or pulsing in the forming box.

One method (U. S. Pat. No. 4,494,278) for reducing or eliminating these problems was to mill the fluff and air convey it to the forming hood with general disregard for clumping. Then, the fiber/air mixture was introduced into an agitated box over the forming wire. The fibers were then redistributed and sifted through a screen before falling onto the wire to form the pad.

In other formers, fibers are conveyed to hoppers which feed secondary milling rotors immediately above the forming area. This and the '278 method both overcome the problems listed but require significantly more equipment than the simple forming box.

The current invention is aimed at a simple and cost effective means for forming uniform fluff pads with high pad integrity. This is advantageously applied to a drum style former—but for wire forming, it is possible to position the hammermill directly over the wire and avoid many of the problems listed above.

In one preferred embodiment, the invention includes a frame providing a longitudinally extending path, a drum mounted on the frame having a circumferentially extending screen, means for rotating the drum in one direction, a vacuum source associated with the frame for maintaining a vacuum inside the drum, a fluff mill in the path on one side of the drum to provide (with the vacuum source) a fluff particle stream, a take-away conveyor in the path on the other side of the drum, a plurality of longitudinally extending fluff delivery ducts on the frame in the path each having a first end connected to the mill and a second end communicating with the screen, the duct second end including a reverse bend section elongated in the direction of drum rotation whereby the outer side of side reverse bend densifies the fluff particle steam thereagainst to achieve fluff particle deposit on the screen without substantial turbulence.

The invention is described in conjunction with an illustrative embodiment in the accompanying drawing, in which FIG. 1 is a side elevational view of apparatus employed in the practice of the invention;

FIG. 3 is an enlarged sectional view taken along the line 3—3 of FIG. 1.

DETAILED DESCRIPTION

Figure 1:
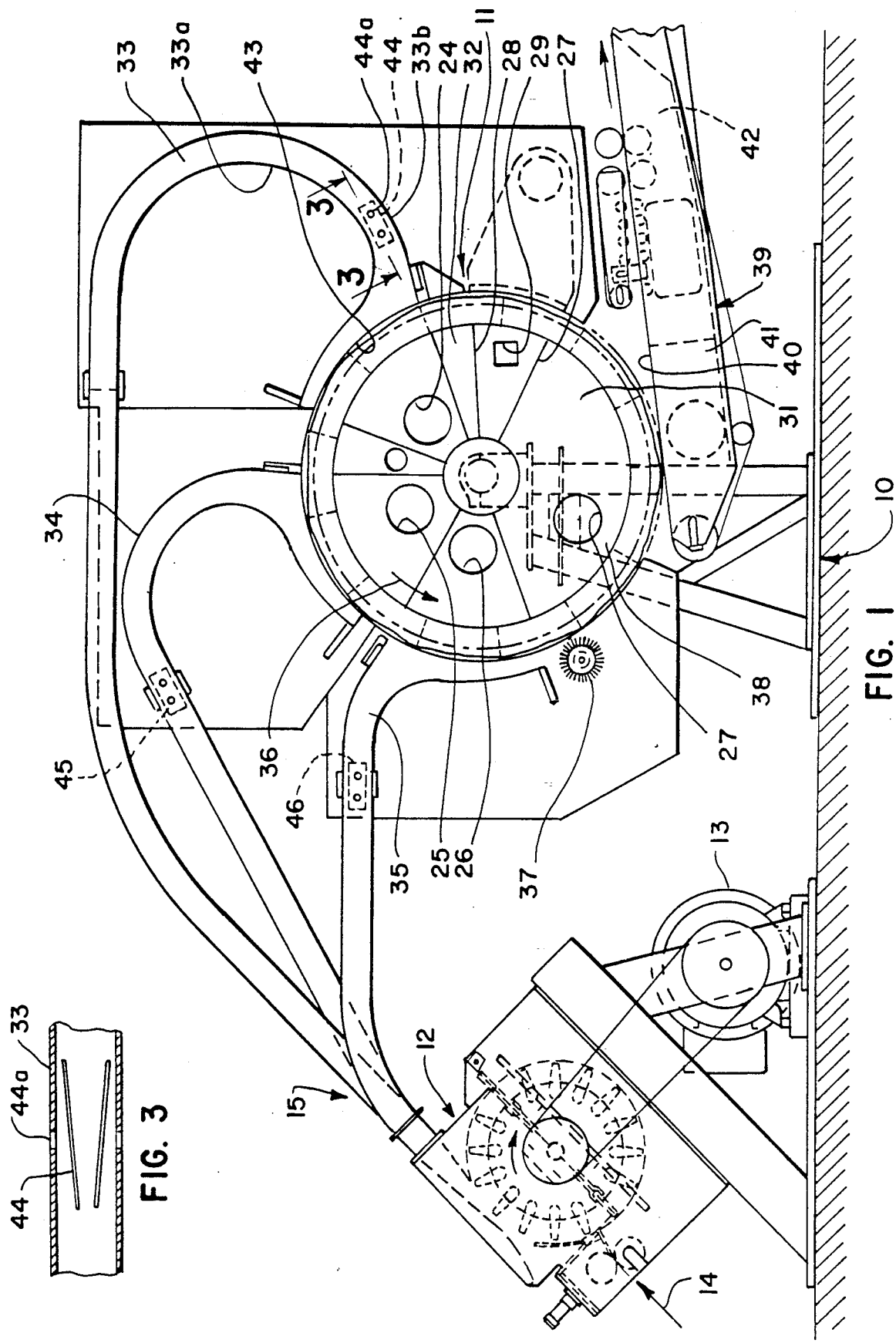

Referring first to FIG. 1, the numeral 10 designates generally a frame for rotatably supporting an annular drum generally designated 11 and which is operably associated with a hammermill generally designated 12. The hammermill is powered by a motor 13 and, in the illustration given, receives a pulp web as at 14 (see the extreme left of FIG. 1) and delivers the same through a plurality of ducts generally designated 15.

More particularly, the annular drum 11 includes a spider 16 (see the left hand portion of FIG. 2) which is supported by a drive shaft 17 carried in ball bearing pillow blocks as at 18 and 19—all being part of the frame 10. A drive is indicated schematically at 20 in the form of a sheave operably associated with a drive motor and belt (not shown).

Figure 2:
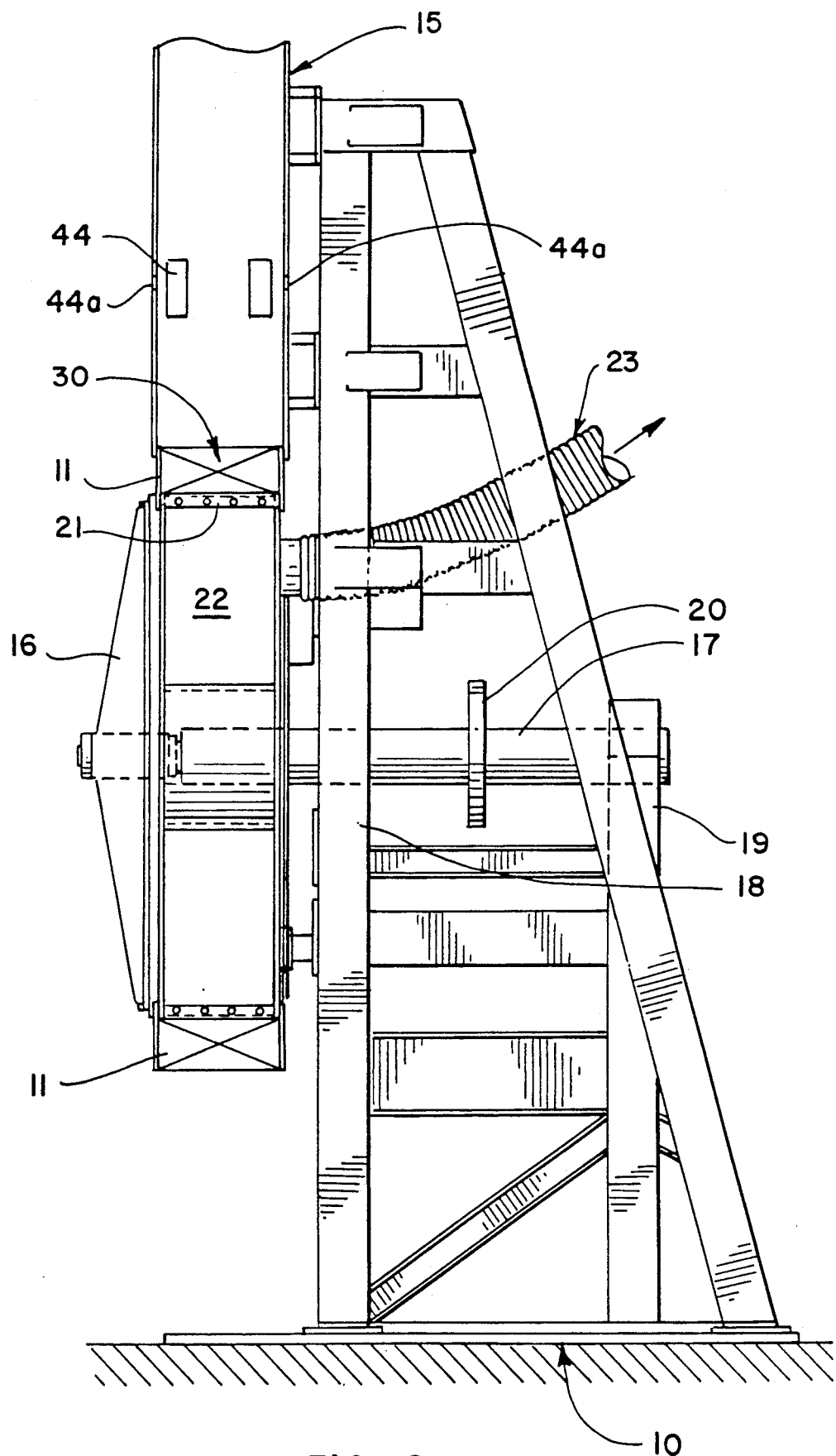
FIG. 2 is an end elevational view of the apparatus of FIG. 1.

Still referring to FIG. 2 the inner wall of the annular drum 11 as at 21 is sealingly related to a plenum 22, portions of which are exhausted by a vacuum connection generally designated 23. Only one such connection is shown in FIG. 2 but in the illustrated embodiment as seen in FIG. 1, we provide four vacuum ports as at 24, 25, 26 and 27. Radial vanes are provided at a plurality of angularly related positions, a first of which is designated 27. The vane 27 in the stationary plenum 22 along with a second vane 28 defines a chamber for introducing air through the inlet port 29 which is used for cleaning the screen. The screen provided in the annular drum is schematically represented at 30 in FIG. 2. Chambers as at 31 and 32 (now referring to FIG. 1) and which flank the chamber with the air inlet opening 29 are unused, being neither under pressure nor vacuum.

Streams of fluff particles are introduced through the ducts 33, 34 and 35 which are relatively elongated at their outlet ends in the direction of screen movement, i.e., rotation of the annular drum 11 as indicated by the arrow in the central part of FIG. 1 and which is designated 36.

After the fluff has been deposited on the screen 30 of the annular drum 11 from the three ducts 33-35, the now-formed fluff pads pass by a scarfing wheel 37 rotatably mounted on the frame in conventional fashion.

We provide a baffle for the vacuum as at 38 to reduce the holding force on the pads so that the pads can be stripped by a takeaway conveyor 39 movably mounted on the frame 10. The takeaway conveyor 39 includes an endless belt 40 which advantageously is foraminous or otherwise air permeable to allow vacuum to draw the pads from the drum 11. A first vacuum chamber is provided as at 41 and a second vacuum chamber as at 42 as part of the takeaway conveyor.

We have found the structure of the fluff-supply ducts to be especially advantageous in achieving the benefits of the invention. More particularly, in order to stabilize the air mass in the forming section, the fiber/air mixture is separated into multiple ducts in route to the pad former. This allows smaller cross-sections and avoids unstable air behaviors.

Prior to fiber laydown the duct curvature causes the fiber/air mixture to stratify; i.e., the fiber density is higher than air and thus the fiber concentration at the outside of the curve is greater than than at the inside of the curve. The high concentration portion of the flow is directed at a small angle from normal (approximately perpendicular) to the forming wire (pad form) and at high velocity without turbulent mixing. The lower concentration portion (inside track) is slowed down by an expansion of the duct area. Design parameters for the duct shapes can be generally described as:

cross sectional areas are set to maintain flow velocities in the range of 40 to 200 feet per second;

changes in direction are gradual; i.e., radii of curvature are typically greater than four times the duct height;

high concentration flow area (outside of duct curve) is directed roughly normal to the forming surface;

final shape of the "inside" curve follows natural expansion of air flow stream into chamber;

In addition to the improved air flow stability, the invention also offers the benefits of;

space between separate forming sections, i.e., duct outlets, for introduction of superabsorbent powder into a specific layer of the pad;

potential to make multi layer pads of dissimilar fluff materials;

ability to tailor forming air flows for start of pad formation (high volume/low pressure) separate from end of pad formation (low volume/high pressure).

DUCT CONSTRUCTION

We have found it particularly advantageous to construct the delivery duct work in two different cross sectional areas adjacent the discharge end—as can be readily appreciated from a consideration of FIG. 1. There each duct 33–35 is seen to include a reverse bend or general C-shape with the bottom of the C-shape being relatively elongated and open to the screen 30 on the drum 11. More particularly the inner side of each duct as at 33a (relative to the duct 33) is generally C-shaped whereas the outer side as at 33b is only partially C-shaped to provide the discharge end of the duct work with an opening as at 43 facing the screen. As mentioned previously the outer side 33b of the reverse bend section achieves a densification of the particle stream adjacent to itself so as to develop a deposition of the fluff particles on the screen without substantial turbulence.

Preferably, we include within the ducts deflector means as at 44, 45 and 46 relative to the ducts 33–35, respectively. Typical deflectors are seen at 44 in FIGS. 2 and 3 and include plates extending generally longitudinally of the ducts and convergent relative to each other in the direction of the fluff particle stream. Air is drawn in through openings as at 44a relative to the deflector means 44 and similar openings are provided for the deflectors 45 and 46. These deflectors 44–46 advantageously concentrate the deposition of fluff particles centrally of the width of the diaper shape which is the area most likely for receipt for excreta of infants and incontinent adults.

OPERATION

In the operation of the invention, a pulp web 14 is milled into fluff particles by the hammermill 12 and drawn through ducts 33–35 under the influence of vacuum applied as at 23 (see FIG. 2) to a stationary plenum 22. Moving past the open ends of the ducts as at 43 relative to the duct 33 (see FIG. 1) is a screen which advantageously may be in the form of an annular drum 11. Suitable forms to shape the deposited fluff particles into hourglass shaped pads are provided as part of the screen 30.

The significant factor we have found is that turbulence is eliminated by having a gradual change in direction of the particle flow by virtue of the curvature at 33b in the leg portion of the duct and then continuing the duct into a foot-like portion overlying the annular drum 11. This results in a stratification of the fluff particles with the more concentrated or dense particles being on the outside of the curve or reverse bend so as to impinge upon the screen at a slight angle to perpendicular.

While in the foregoing specification a detailed description of an embodiment of the invention has been set down for the purpose of explanation, many variations in the details hereingiven may be made by those skilled in the art without departing from the spirit and scope of the invention.

We claim:

1. A fluff former comprising a frame providing a longitudinally extending path, a drum mounted in said frame having a circumferentially extending screen, means for rotating said drum one direction, a vacuum source associated with said frame for maintaining a vacuum inside said drum, fluff mill means in said path on one side of said drum to provide with said vacuum source a fluff particle stream, a take-away conveyor in said path on the other side of said drum, a plurality of longitudinally extending fluff delivery ducts on said frame in said path each having a first end connected to said mill means and a second end communicating with said screen, each said duct adjacent said second end including a generally C-shaped section to change the direction of flow of said stream, said generally C-shaped section having an inner side and an outer side, said inner side being elongated in the direction of drum rotation and said outer side extending generally perpendicularly of said screen whereby the outer side densifies the fluff particle stream thereagainst to achieve fluff particle deposit on said screen.

2. The structure of claim 1 in which each generally C-shaped section is characterized by a radius of curvature which is at least about four times the duct height measured in the direction of the radius of curvature.

3. A fluff former comprising a frame providing a longitudinally extending path, a drum mounted in said frame having a circumferentially extending screen, means for rotating said drum one direction, a vacuum source associated with said frame for maintaining a vacuum inside said drum fluff mill means in said path on one side of said drum to provide with said vacuum source a fluff particle stream, a take-away conveyor in said path on the other side of said rum, a plurality of longitudinally extending fluff delivery ducts on said frame in said path each having a first end connected to said mill means and a second end communicating with said screen, each said duct adjacent said second end including generally C-shaped section to change the direction of flow of said stream, said generally C-shaped section having an inner side and an outer side, said inner side being elongated in the direction of drum rotation and said outer side extending generally perpendicularly of said screen whereby the outer side densifies the fluff particle stream thereagainst to achieve fluff particle deposit on said screen, each duct having a cross-sectional area such as to maintain flow velocities in the range of about 40 to about 200 feet per second.

4. A fluff former comprising a frame providing a longitudinally extending path, a drum mounted in said frame having circumferentially extending screen, means for rotating said drum one direction, a vacuum source associated with said frame for maintaining a vacuum inside said drum, fluff mill means in said path on one side of said drum to provide with said vacuum source a fluff particle stream, a take-away conveyor on in said path on the other side of said drum, a plurality of longitudinally extending fluff delivery ducts on said frame in said path each having a first end connected to said mill means and a second end communicating with said screen, each said duct adjacent said second end having a generally C-shaped section having inner and outer ends, said section having first in the direction of stream flow a substantially uniform cross section leg portion and thereafter adjacent said second end a foot-like portion elongated in the direction of drum rotation, said foot-like portion having a wall first in the direction of drum rotation extending generally perpendicularly of said screen.

5. A fluff former comprising a frame providing a longitudinally extending path, a drum mounted in said frame having a circumferentially extending screen, means for rotating said drum one direction, a vacuum source associated with said frame for maintaining a vacuum inside said drum, fluff mill means in said path on one side of said drum to provide with said vacuum source a fluff particle stream, a take-away conveyor on in said path on the other side of said drum, a plurality of longitudinally extending fluff delivery ducts on said frame in said path each having a first end connected to said mill means and a second end communicating with said screen, each said duct adjacent said second end having a generally C-shaped section having inner and outer ends, said section having first in the direction of stream flow a substantially uniform cross section leg portion and thereafter adjacent said second end a foot-like portion elongated in the direction of drum rotation, each duct in the uniform cross section thereof is equipped with deflector means for concentrating the deposit of fluff particles centrally of the width, each said duct adjacent said deflector means being equipped with air supply openings, said openings being positioned slightly downstream of the upstream end of each deflector.

6. A fluff former comprising a frame providing a longitudinally extending path, screen means movably mounted on said frame in said path, means for moving said screen means in one direction, a vacuum source associated with said frame for maintaining a vacuum on one side of said screen means, fluff mill means operably associated with said frame to provide with said vacuum source a fluff particle stream, a plurality of longitudinally extending fluff delivery ducts on said frame in said path each having a first end connected to said mill means and a second end communicating with said screen means, each said duct adjacent said second end having a generally C-shaped section having first in the direction of stream flow a substantially uniform cross section leg portion and thereafter adjacent said second end a foot-like portion elongated in the direction of movement of said screen means, said foot-like portion having a wall first in the direction of movement of said screen means extending generally perpendicularly of said screen means.

* * * * *